United States Patent
Beyer et al.

(10) Patent No.: US 9,970,867 B2
(45) Date of Patent: May 15, 2018

(54) METHOD OF DETERMINING THE CONCENTRATION OF A GAS COMPONENT AND SPECTROMETER THEREFOR

(71) Applicant: SICK AG, Waldkirch (DE)

(72) Inventors: Thomas Beyer, Waldkirch (DE); Julian Edler, Waldkirch (DE)

(73) Assignee: SICK AG, Waldkirch (DE)

( * ) Notice: Subject to any disclaimer, the term of this patent is extended or adjusted under 35 U.S.C. 154(b) by 0 days. days.

(21) Appl. No.: 15/223,726

(22) Filed: Jul. 29, 2016

(65) Prior Publication Data

US 2017/0045446 A1 Feb. 16, 2017

(30) Foreign Application Priority Data

Aug. 14, 2015 (EP) ..................... 15181091

(51) Int. Cl.
  *G01N 21/39* (2006.01)
  *G01J 3/10* (2006.01)
  *G01J 3/433* (2006.01)

(52) U.S. Cl.
  CPC ............... *G01N 21/39* (2013.01); *G01J 3/10* (2013.01); *G01J 3/433* (2013.01); *G01J 2003/4332* (2013.01); *G01N 2021/399* (2013.01); *G01N 2201/12* (2013.01)

(58) Field of Classification Search
  CPC ................................ G01N 21/39; G01J 3/433
  USPC ....................................................... 356/437
  See application file for complete search history.

(56) References Cited

U.S. PATENT DOCUMENTS

| 5,285,677 A * | 2/1994 | Oehler ................... G01N 27/74 |
| | | 73/24.01 |
| 5,973,782 A | 10/1999 | Bomse |
| 7,616,316 B1 | 11/2009 | Silver et al. |
| 7,679,059 B2 * | 3/2010 | Zhou ........................ G01J 3/02 |
| | | 250/339.13 |
| 9,074,930 B2 * | 7/2015 | Kaufmann .............. G01J 3/108 |
| 9,453,765 B2 * | 9/2016 | Depenheuer .............. G01J 3/42 |
| 2011/0150035 A1 | 6/2011 | Hanson et al. |

(Continued)

FOREIGN PATENT DOCUMENTS

| DE | 102 38 356 A1 | 1/2004 |
| DE | 10 2012 223 874 B3 | 5/2014 |

OTHER PUBLICATIONS

Silver, Joel A., "Frequency-modulation spectroscopy for trace species detection: theory and comparison among experimental methods", Applied Optics, Feb. 20, 1992, pp. 707-717, vol. 31, No. 6.

(Continued)

*Primary Examiner* — Roy M Punnoose
(74) *Attorney, Agent, or Firm* — Nath, Goldberg & Meyer; Jerald L. Meyer; Stanley N. Protigal

(57) ABSTRACT

The invention relates to a method and to a spectrometer for determining the concentration of a gas component, wherein a light source of the spectrometer is operated as in wavelength modulation spectroscopy (WMS). Thus a determination of the concentration can also take place in accordance with WMS and the measured data can, however, additionally be processed, namely a sorting takes place on the time axis, such that the concentration can be determined using the methods of direct absorption spectroscopy (DAS).

19 Claims, 5 Drawing Sheets

(56) References Cited

U.S. PATENT DOCUMENTS

| | | | | |
|---|---|---|---|---|
| 2012/0283961 A1* | 11/2012 | Wittmann | ............... | G01N 21/39 |
| | | | | 702/24 |
| 2014/0185035 A1* | 7/2014 | Depenheuer | .............. | G01J 3/42 |
| | | | | 356/73 |
| 2014/0299774 A1* | 10/2014 | Kaufmann | ............... | G01J 3/108 |
| | | | | 250/339.07 |
| 2014/0340684 A1* | 11/2014 | Edler | .................... | G01J 3/4338 |
| | | | | 356/409 |
| 2015/0338339 A1* | 11/2015 | Hutchings | .......... | G01N 21/3504 |
| | | | | 356/437 |
| 2015/0338342 A1* | 11/2015 | Muramatsu | ............ | G01N 21/39 |
| | | | | 356/409 |
| 2016/0084757 A1* | 3/2016 | Miron | .................... | G01N 21/39 |
| | | | | 356/437 |

OTHER PUBLICATIONS

Search report issued in corresponding European application No. 15 18 1091 dated Mar. 4, 2016.

* cited by examiner

METHOD OF DETERMINING THE CONCENTRATION OF A GAS COMPONENT AND SPECTROMETER THEREFOR

FIELD OF THE INVENTION

The invention relates to a method of determining the concentration of a gas component and to a spectrometer for carrying out the method.

BACKGROUND

Various methods are known for determining the concentration of a gas component of a measurement gas. They include direct absorption spectroscopy (DAS) and wavelength modulation spectroscopy (WMS).

In direct absorption spectroscopy, the wavelength of a laser is varied via a current ramp and the detector signal is recorded. Light is absorbed by the measurement gas in accordance with the Beer-Lambert law when running through the current ramp when the laser passes through the region of the absorption line.

$$I = I_0 * e^{-\alpha(\lambda) cL}$$

$\alpha(\lambda)$ is the absorption dependent on the wavelength;
c is the gas concentration;
and L is the path over which the gas absorbs.

The detector signal is thereby deformed such that in comparison with the detector signal without gas absorption an absorption line can be recognized which can then e.g. be fit by a fit with a physical model function (a Voigt absorption line as a rule) and the absorption surface (surface below the absorption curve) can be determined which is proportional to the gas concentration.

Further evaluation processes of direct absorption spectroscopy are also known in which, for example, the surface below the absorption line is determined without physical model functions.

Wavelength modulation spectrometry (WMS) is a form of optical absorption spectroscopy which makes possible a detection of very small optical absorptions because the absorption measurements of small frequencies (near DC) at which the light sources have high noise are shifted toward high frequencies in which shot noise is the limiting factor. This frequency shift can improve the measurement sensitivity by three to five orders of magnitude.

WMS is carried out as a rule using continuously tunable lasers such as diode lasers (TDL). In this respect, the wavelength is tuned slowly over an absorption line of the measurement gas and is additionally lightly modulated by a modulation frequency f, typically sinusoidal, with is high in comparison. When the light beam which is wavelength-modulated in this manner propagates through the measurement path, an amplitude modulation of the light results from the intensity change of the laser and by the absorption of the measurement gas. When the light is then detected in the light receiver and a received signal is produced in dependence on time, the received signal includes AC components at the modulation frequency f and its harmonics 2f, 3f, 4f, etc. One of the AC components can be selected for the evaluation and can be evaluated in a phase-sensitive process, e.g. using a lock-in process. This process is also called demodulation. The signal obtained at the frequency nf on a demodulation is called an nf signal (n=1, 2, 3, . . . ). The demodulated signal thus includes information with respect to the optical absorption and the intensity of the light beam. Concentrations of a gas component of the examined measurement gas can be determined via the absorption measured in this manner.

A detailed theory which describes WMS and the relationships between the shape of the absorption line and the shape of the demodulated signal is given in "Frequency-modulation spectroscopy for trace species detection: theory and comparison among experimental methods," Applied Optics 31, 707-717 (1992). The signal shape which is obtained in WMS when the absorption line is moved over slowly and the wavelength is simultaneously modulated at the frequency nf corresponds in quality to the nth derivation of the absorption line so that the name derivative absorption spectroscopy is also used for WMS.

A method is known from DE 102 38 356 A1 in which the two measurement processes WMS and DAS are used alternately in consecutive periods and the detected signals are likewise alternately supplied to two separate averaging processes and evaluated. In the WMS evaluation, the results of the DAS evaluation can be used, e.g. for calibration. The calibration freedom of direct absorption spectroscopy and the accuracy of wavelength modulation spectroscopy are thus obtained.

In a method known from U.S. Pat. No. 7,616,316 B2, a switch is made between DAS at high concentrations of the gas component to be measured and WMS at low concentrations thereof. The measurement method which appears the most suitable is therefore respectively used.

Both measurement methods, WMS and DAS, are used simultaneously in DE 10 2012 223 874 B3 or are used alternately as in DE 102 38 356 A1 and the two measurement results are linked by averaging, whereby smaller errors can be achieved in the result.

The invention has the objective of increasing the functional safety which can be defined with the aid of the so-called safety-integrated level (SIL) in gas concentration determinations to be able to satisfy safety standards which define a specific SIL level. It is possible that an error tolerance of 1 is required in the functional safety. This normally relates to the hardware. Independently of the hardware used, non-random errors can, however, occur in the gas concentration measurement due to external influences such as intensity fluctuations, pressure changes, pressure, temperature and interference. It is therefore the object of the invention to provide a method improved with respect to the functional safety and spectrometers for determining a gas component.

Such an increase in safety could be achieved by using two different measurement methods, DAS and WMS, as known from DE 102 38 356 A1 and DE 10 2012 223 874 B3. It is, however, disadvantageous that this means a doubling of the effort with respect to time and apparatus. In the simultaneous application of the measurement methods disclosed in DE 10 2012 223 874 B3, the laser has to be controlled using a ramp plus sinusoidal modulation. This is disadvantageous for DAS for the direct detector signal in WMS is not suitable for an evaluation according to DAS since the sinusoidal modulation not only produces a power modulation, but also a wavelength modulation. The absorption is also scattered by the sinusoidal modulation after an averaging over e.g. a sinusoidal period and the evaluation is difficult and can no longer be achieved via a fit using a physical model. The result of such a DAS is therefore not as significant since the laser is controlled in an unfavorable manner for this purpose.

SUMMARY

The method in accordance with the invention for determining the concentration of a gas component comprises the following steps in the first alternative:

producing a light beam having a wavelength variable in a wavelength range ([$\lambda 1, \lambda 2$]);
guiding the light beam through a measurement volume in which the gas component to be determined is present, wherein the gas component has an absorption in the wavelength range;
tuning the wavelength range, wherein an additional modulation of the wavelength takes place during the tuning at a modulation frequency (f) which is high in comparison with the tuning rate so that a wavelength-to-time progression with a high-frequency modulation results;
detecting the intensity of the light beam after passing through the measurement volume;
during the tuning, detecting measurement points which contain an intensity value and which are each recorded at times which correspond to the same phasing of the modulation;
producing an artificial measurement curve from the detected measurement points; and
evaluating the artificial measurement curve and determining a first concentration value therefrom.

The method comprises the following steps in the second alternative:
producing a light beam having a wavelength variable in a wavelength range ([$\lambda 1, \lambda 2$]);
guiding the light beam through a measurement volume in which the gas component to be determined is present, wherein the gas component has an absorption in the wavelength range;
tuning the wavelength range, wherein an additional modulation of the wavelength takes place during the tuning at a modulation frequency (f) which is high in comparison with the tuning so that a wavelength-to-time progression with a high-frequency modulation results;
detecting the intensity of the light beam after passing through the measurement volume;
during the tuning, saving measurement points which each comprise a time and an associated intensity value;
producing an artificial measurement curve from the saved measurement points by shifting the measurement points on the time axis;
with the shift taking place such that an artificial, linear progression results after the shift in the wavelength-to-time progression; and
evaluating the artificial measurement curve and determining a first concentration value therefrom.

The artificial measurement curve is preferably created such that the first concentration value can be determined from it in accordance with the methods of direct absorption spectroscopy.

The essential idea is thus the carrying out of only one measurement, and indeed with a control of the laser, that is a tuning of the wavelength range, for measurement in accordance with WMS. The measured signals obtained can then, however, be evaluated in accordance with two different methods, that is e.g. DAS and WMS. Two results can be obtained in two different ways in this manner. This is only possible by the detection of the measurement points and by a new sequence of the measurement points in order, however, to produce an artificial measurement curve from the previous measured values which can then preferably be evaluated in accordance with DAS. This contains the essential idea:

In the first alternative, the artificial measurement curve is obtained from the measurement points having the same phasing and in the second alternative it is obtained in a somewhat more laborious way via the shifting of (all) the measurement points on the time scale, that is the new sequence.

The essential advantage of such a method is that the evaluation of a detector signal is possible using two different evaluation methods so that external influences cannot produce any non-random errors, whereby a high SIL level can be reached.

To reach a specific SIL level, it is sensible to obtain a second concentration value, which is done in a further development of the invention in that an evaluation of the original measurement curve in accordance with the methods of wavelength modulation spectroscopy is carried out after the detection and saving of the measurement points and a second concentration value is determined.

The two produced concentration values can thus be used to reach a higher level with respect to functional safety by a validation of the values with respect to one another.

The two concentration values obtained in the different ways can be compared with one another in order thus to use one of the two values only for the verification of the other.

Additionally or alternatively, a common concentration value can be produced by averaging from the two concentration values and then has a smaller error than a single value.

The object is also satisfied by two alternative spectrometers each corresponding to the two alternative methods.

In the first alternative the spectrometer comprises:
a light source for producing a light beam having a wavelength variable in a wavelength range ([$\lambda 1, \lambda 2$]);
a measurement volume in which the gas component to be determined is present and through which the light beam runs;
control means for the light source for tuning the wavelength range, wherein an additional modulation of the wavelength takes place during the tuning at a modulation frequency (f) which is high in comparison with the tuning so that a wavelength-to-time progression with a high-frequency modulation results;
a light detector for detecting the intensity of the light beam after passing through the measurement volume;
storage means for saving measurement points during the turning, wherein the measurement points include an intensity value and are each recorded at different times which correspond to the same phasing of the modulation;
an evaluation unit which is adapted
to carry out the method in the first alternative;
and to produce an artificial measurement curve from the saved measurement points; and
to evaluate the artificial measurement curve and to determine a first concentration value therefrom.

In the second alternative the spectrometer comprises:
a light source for producing a light beam having a wavelength variable in a wavelength range ([$\lambda 1, \lambda 2$]);
a measurement volume in which the gas component to be determined is present and through which the light beam runs;
control means for the light source for tuning the wavelength range, wherein an additional modulation of the wavelength takes place during the tuning at a modulation frequency (f) which is high in comparison with the tuning so that a wavelength-to-time progression with a high-frequency modulation results;
a light detector for detecting the intensity of the light beam after passing through the measurement volume;

storage means for saving measurement points which each comprise a time and an associated intensity value during the tuning;

an evaluation unit which is adapted to carry out the method in the second alternative;

and to produce an artificial measurement curve from the saved measurement points by shifting the measurement points on the time axis, wherein the shift takes place such that an artificial, linear progression results after the shift in the wavelength-to-time progression;

and to evaluate the artificial measurement curve and to determine a first concentration value therefrom.

In a further development, the light source is a tunable laser whose emission wavelength is variable by a control current or a control voltage.

BRIEF DESCRIPTION OF THE DRAWINGS

The invention will be explained in detail in the following with reference to an embodiment and to the drawing. There are shown in the drawing.

DETAILED DESCRIPTION

Figure 1:
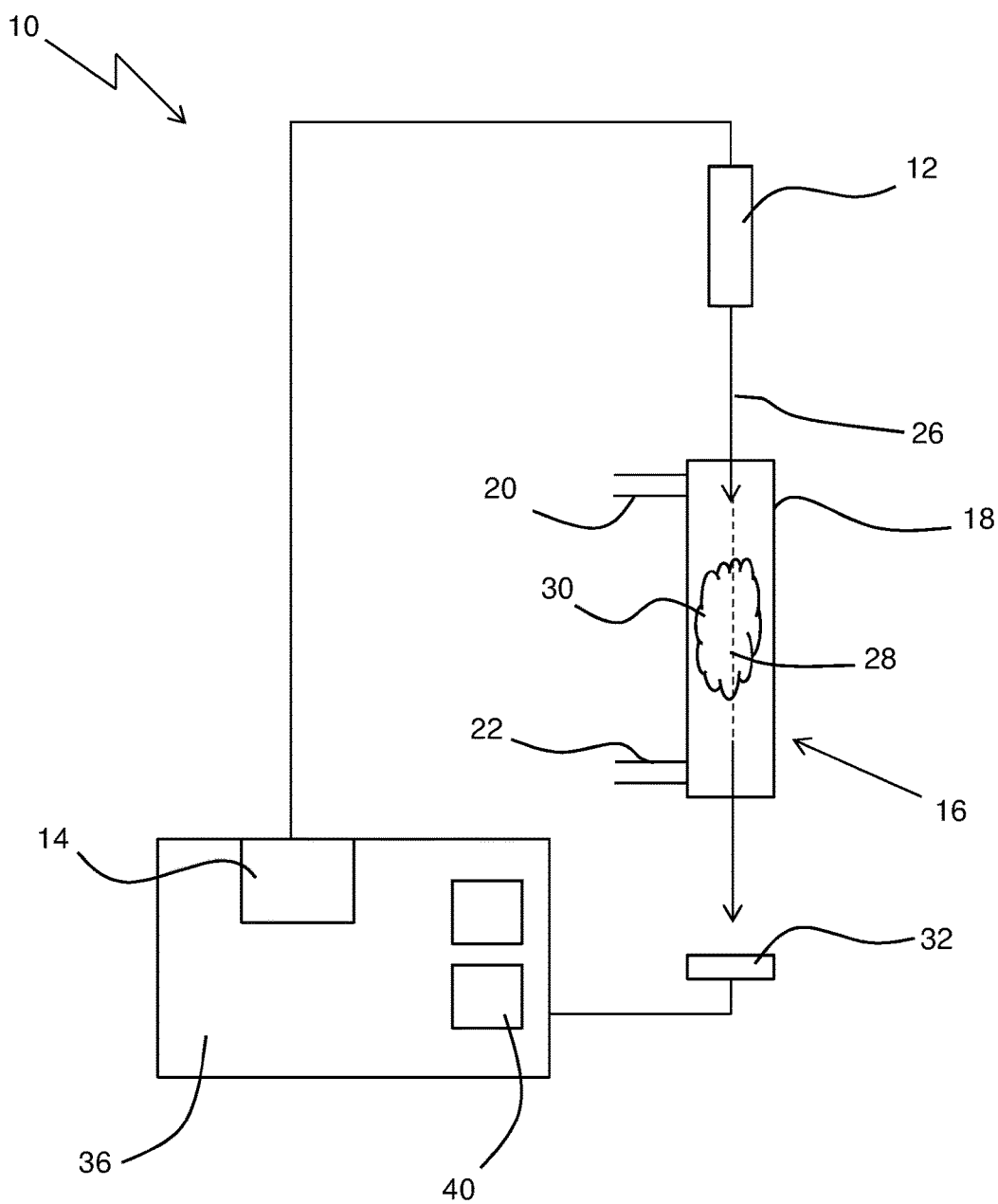
FIG. 1 a schematic representation of the spectrometer in accordance with the invention.

A spectrometer 10 in accordance with the invention shown schematically in FIG. 1 has a light source 12 which is preferably configured as a tunable diode laser (TDL) which is controllable by control means 14. The tuning range corresponds to a wavelength range [λ1, λ2]. A control current IA is applied to the diode layer 12 by the control means 14 for the tuning so that a corresponding wavelength λ is produced in dependence on the current. The current IA of the control current is applied in dependence on the time t in FIG. 2. If the current IA changes, the wavelength λ also changes, as should be indicated by the two ordinate axes in FIG. 2.

The spectrometer 10 furthermore has a measurement volume 16 which can be formed from a measurement cell 18 having a measurement gas inlet 20 and a measurement gas outlet 22. Other arrangements, e.g. open systems ("open path") or systems connected to a pipe which conducts the measurement gas ("cross duct") are also conceivable. A measurement gas 30 is present in the measurement cell 18 and has a gas component whose concentration is to be measured.

The light of the laser 12 is coupled into the measurement cell 18. The optical path within the measurement cell forms an optical measurement path 28. The optical path can be extended via one or more reflectors inside or outside the measurement cell, for example in the form of a White cell or a Herriott cell, in order thus to obtain a longer optical measurement path 28.

Figure 3:
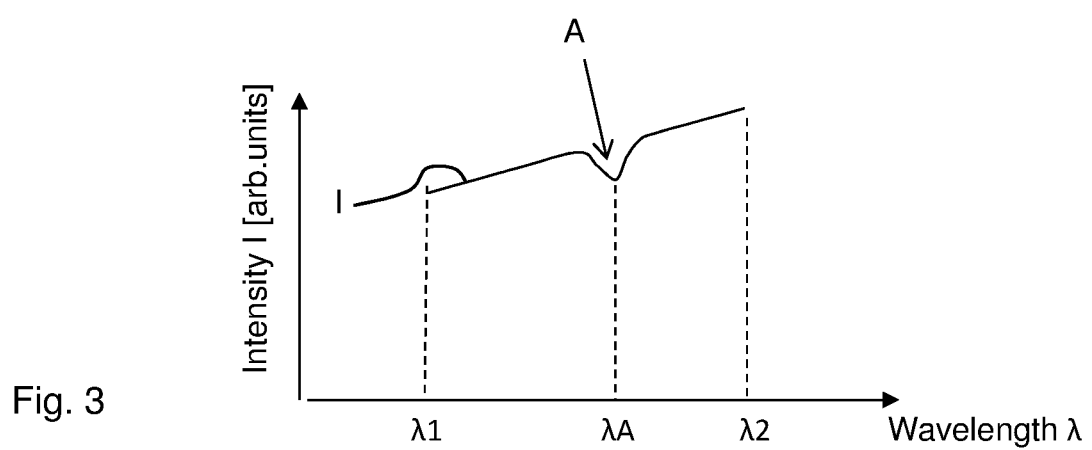
FIG. 3 a qualitative, schematic representation of an absorption signal of a measurement gas component.

The measurement gas 30 which has the gas component to be measured is present in the measurement cell 18. The gas component has an absorption A in the tunable wavelength range so that the light of the laser 12 passing through the measurement path 28 is absorbed at the absorption wavelength λA. This is shown in FIG. 3 which shows the light intensity I transmitted through the measurement cell 18 in dependence on the wavelength λ.

A light detector 32 is furthermore provided which detects the light which has passed through the measurement path. The detector 32 can be a photodiode, an avalanche photodiode or also a photomultiplier (PM). The light detector 32 produces a received signal in dependence on the intensity of the incident light.

The one electrical received signal then includes all the information. It is optionally amplified and/or filtered and supplied to the evaluation unit 36. The concentrations of the gas component are ultimately determined in the evaluation unit 36 from the one received signal.

The significance of the individual components whose particular embodiments and functions will become clear in the following description when the methods in accordance with the invention and the function of the spectrometer 10 in accordance with the invention will be described. It is assumed in this respect that the functions of DAS and WMS such as were briefly initially explained are known in principle.

In accordance with the invention, the tunable laser 12 is controlled by means of control means 38. The control takes place via the control current IA as a rule with diode lasers. The laser emits a specific wavelength λ in accordance with the control current IA. The laser 12 controlled in this manner covers the wavelength [λ1, λ2] (FIGS. 2 and 3).

Figure 2:
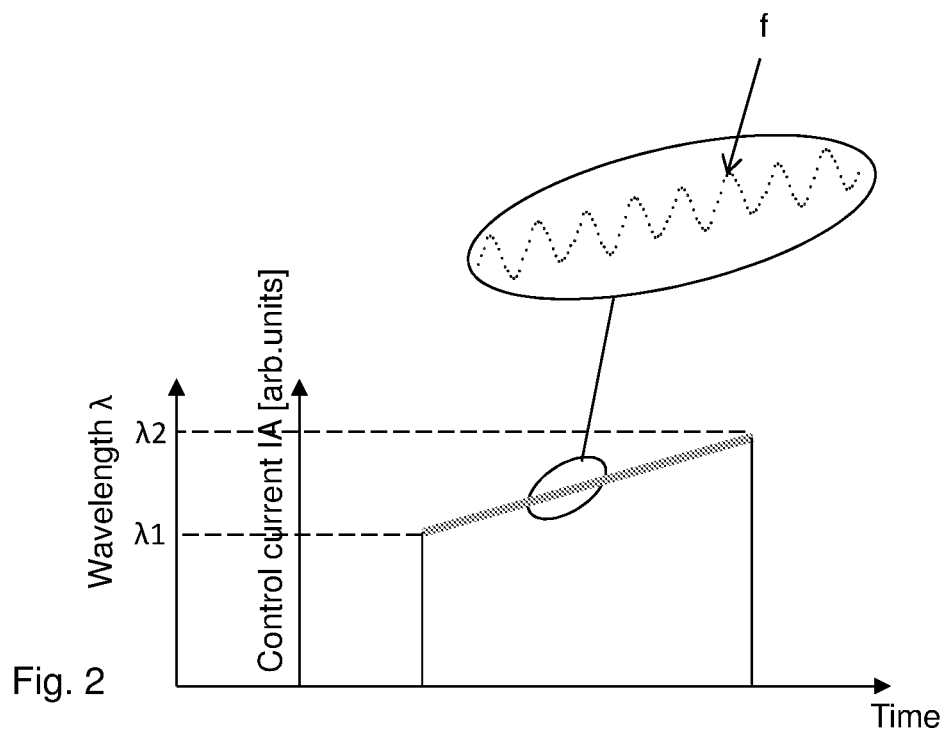
FIG. 2 a qualitative, schematic representation of the laser control.

The control of the laser 12 takes place using a current ramp such as is shown in FIG. 2 on which a modulation is additionally modulated whose frequency f is large with respect to the tuning rate and whose amplitude is small as a rule. This is the typical control for a WMS. FIG. 2 shows the wavelength-to-time diagram resulting from this. A linear ramp can be recognized which additionally shows the high frequency modulation f with a small amplitude. The small amplitude and the high frequency f can only be recognized in the enlarged detail in FIG. 2.

The current ramp with the modulation applied to it is run through repeatedly at a repetition rate for the actual measurement and the measurement is thus repeated at the repetition frequency.

A concentration value which is called a second concentration value within the framework of this application is naturally obtained in a known manner after an evaluation in accordance with the WMS method using this control for a WMS.

The invention now relates to the use of the measured data in order also to obtain a further concentration value, which is called a first concentration value within the framework of this application, in another manner of the evaluation, that is not with a WMS evaluation. And the measured data are indeed processed in a skilled manner such that an evaluation is preferably possible in accordance with the methods of DAS. The invention provides two alternative ways to be able to have an evaluation according to DAS from the measured data.

Figure 4:
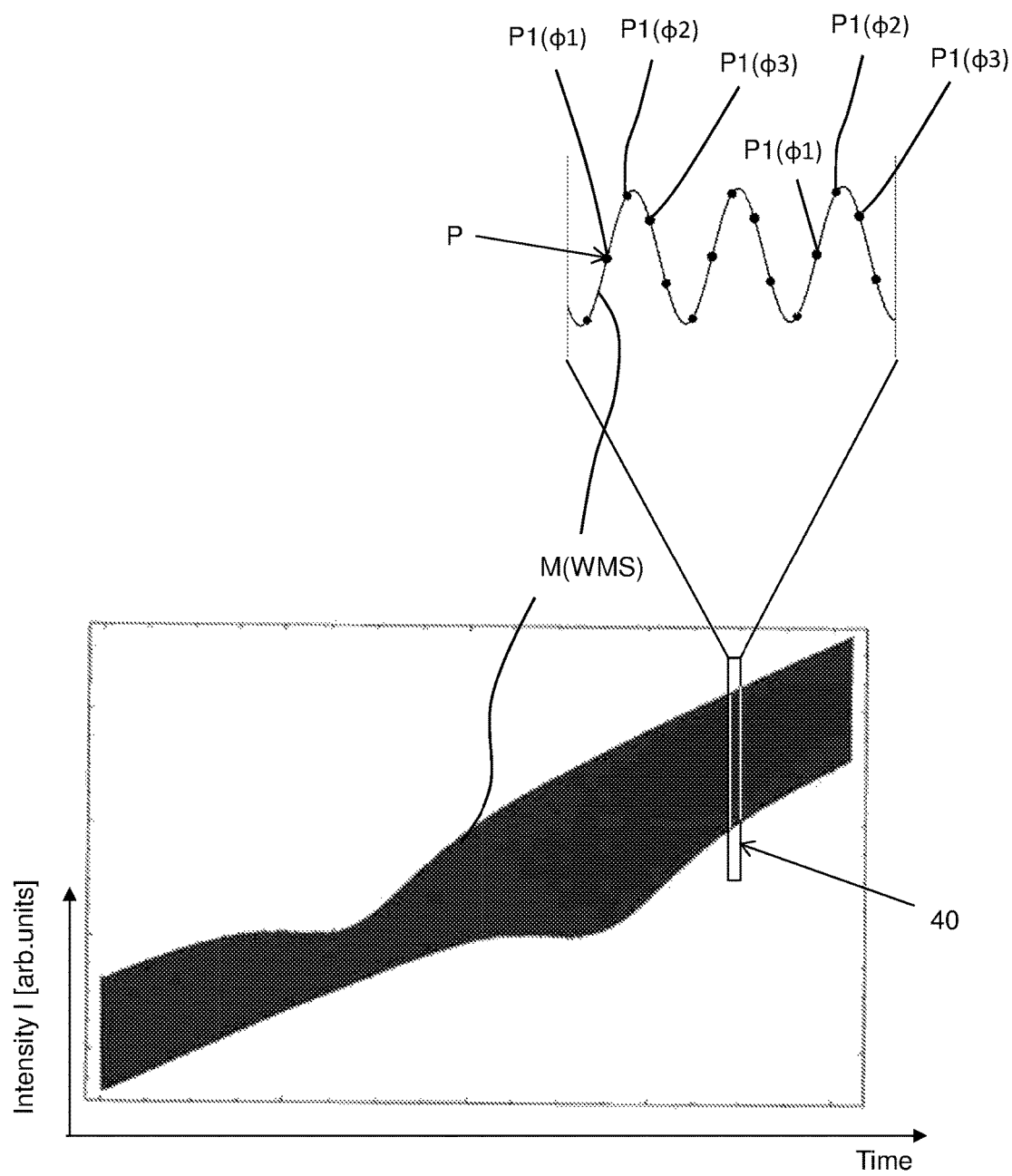
FIG. 4 a representation such as in FIG. 2 after a shift of the points on the time scale.

When controlling the laser in accordance with WMS, as shown qualitatively in FIG. 2, a measurement curve results such as is shown qualitatively in FIG. 4 and which is designated by M(WMS) and as is known from WMS. The band which appears as black in the representation of FIG. 4 actually consists of individual measurement points P which are recorded at specific times and which can only be recognized in an enlarged detail representation of a detail 40.

Figure 5:
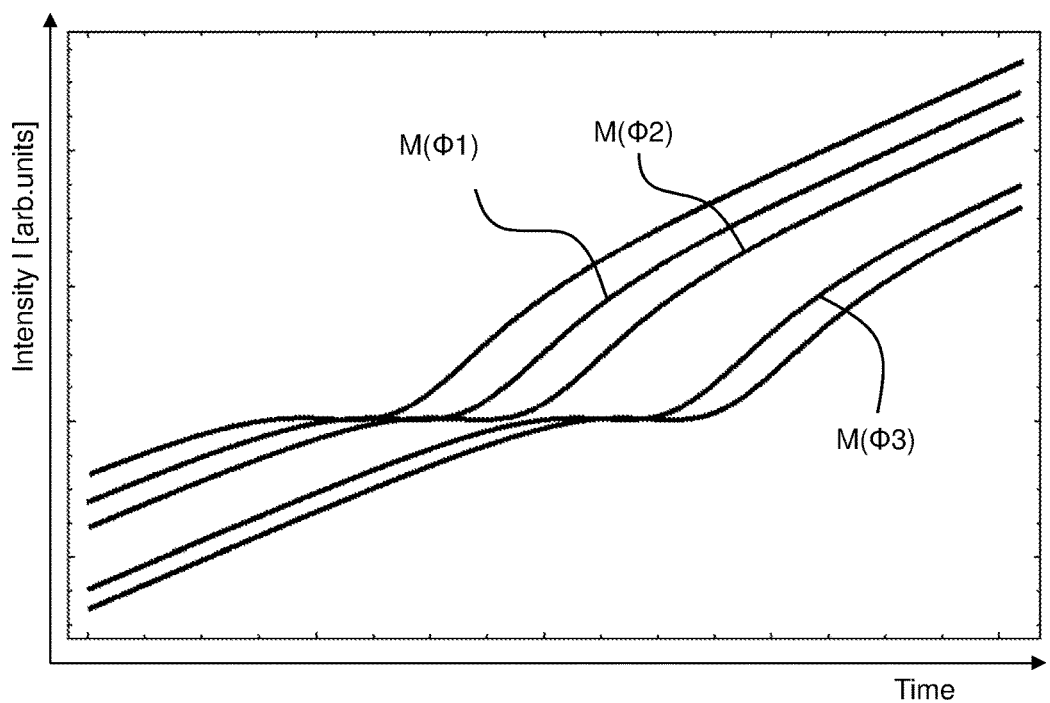
FIG. 5 a representation of a detail from FIG. 4 to illustrate the shift of the points on the time scale.

In the first alternative, measurement points P of the same phase are always detected on the passing through of the measurement region and are saved in a store 40. Measurement points P are therefore e.g. always detected at a phase ϕ1 which are here called measurement points P1(ϕ1). If these measurement points P1(ϕ1) are looked at separately, an artificial measurement curve M(ϕ1) results such as is shown in FIG. 5. This artificial measurement curve corresponds to that which is known from DAS so that it shows the absorption and the first concentration value could already be determined from it.

Figure 6:
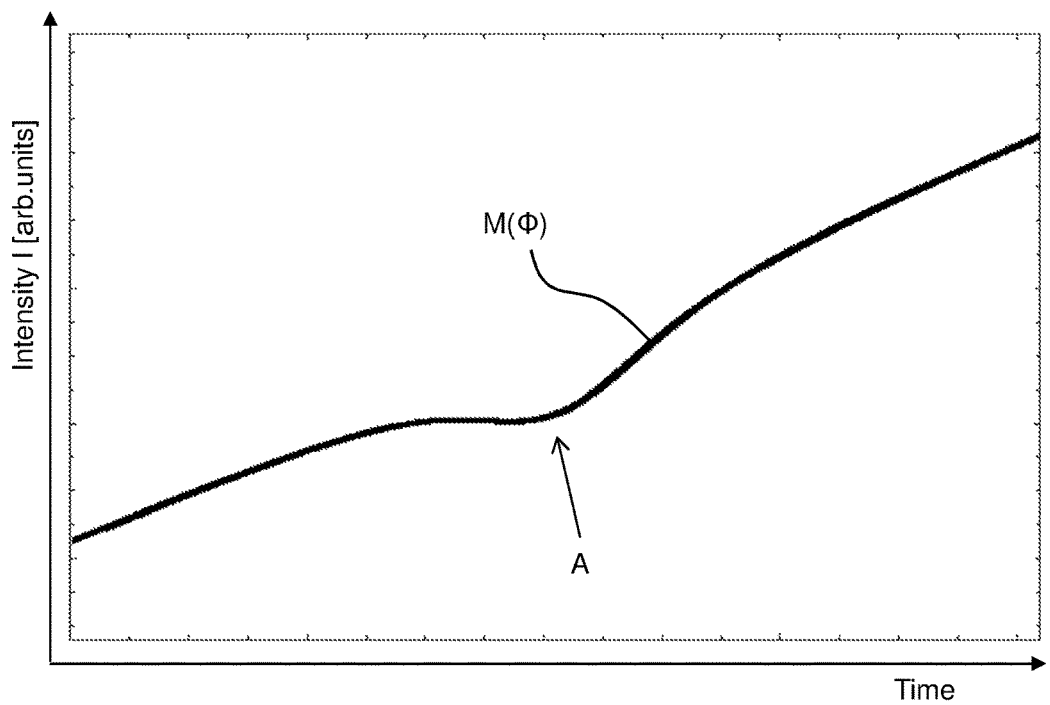
FIG. 6 a representation such as in FIG. 3 of the artificial measurement curve after a shift of the points on the time scale.

To increase the accuracy, a plurality of such artificial measurement curves are each recorded in an analog manner at different phases, e.g. at ϕ2 and ϕ3. A family of artificial measurement curves are thus obtained of which three are designated by M(ϕ1), M(ϕ2) and M(ϕ3) in FIG. 5. These measurement curves can now be combined to form a sum measurement curve M(ϕ) by displacement on the time axis (FIG. 6). This sum measurement curve M(ϕ) shows the absorption A from which then ultimately the first concentration value can be determined with a higher accuracy using the known evaluation methods of DAS.

Figure 8:
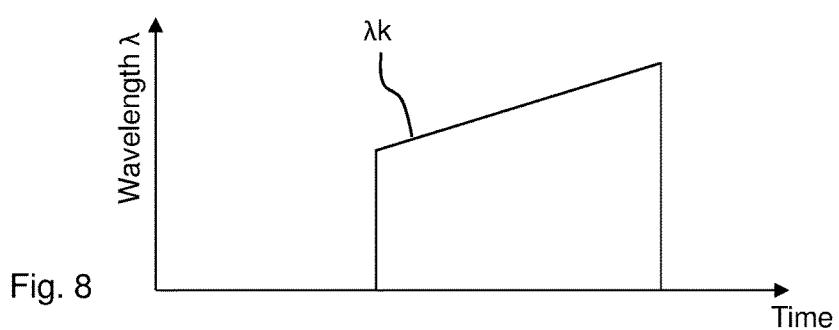
FIG. 8 a time-wavelength diagram of an artificial curve after displacement.

In the second alternative, the measurement points P are first recorded and saved, as in the first alternative, during the tuning. Each measurement point P consists of a time tp (to which then a specific wavelength also corresponds) and of an associated intensity value Ip. All the measurement points are saved in a store 40. A new artificial intensity progression, that is an artificial measurement curve, is produced from these measurement points P of a tuning (from λ1 to λ2). The procedure is as follows in this respect: The measurement points P on the time axis (abscissa) are displaced and are so-to-say arranged in a new sequence or are, in other words, "resorted". The displacement takes place in this respect such that a linear progression λk results, as shown in FIG. 8, after the displacement (new sequencing) in the resulting wavelength-to-time diagram. The additional high frequency modulation f is then no longer present.

Figure 7:
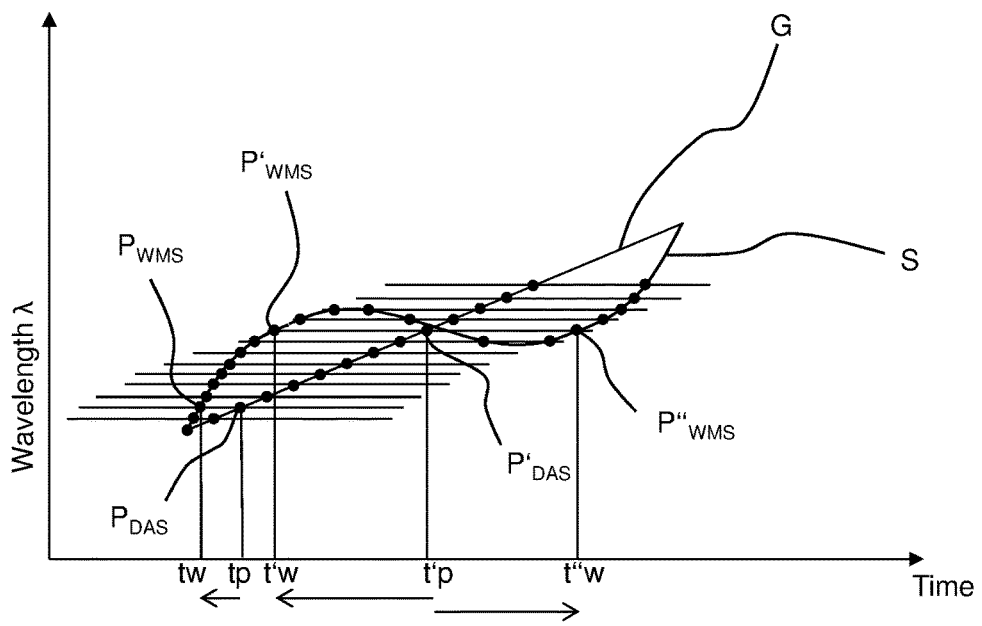
FIG. 7 a cutout of a time-wavelength diagram for explaining the displacement.

The displacement (resorting or new sequencing) will be explained with reference to FIG. 7. Only a small detail from the wavelength-to-time diagram of FIG. 2 is shown there. The points $P_{WMS}$ or $P'_{WMS}$, $P''_{WMS}$ drawn in FIG. 7 are bijectively associated with the saved measurement points P over the times tp. Each point $P_{WMS}$, $P'_{WMS}$, $P''_{WMS}$ thus has a time coordinate tw, t'w and t''w and a wavelength coordinate corresponding to the time coordinate. When tuning with the additional modulation, the points $P_{WMS}$, $P'_{WMS}$, $P''_{WMS}$ lie on the curve S, as FIG. 7 shows.

However, the displacement (new sequencing) now takes place, and indeed such that the straight line G afterward results. This requires a displacement of the point $P_{WMS}$ on the time axis (horizontal) to a new time tp so that the point $P_{WMS}$ is shifted to $P_{DAS}$. This takes place analogously for the other points. To obtain a clean linear progression G, some of the points $P_{WMS}$ have to be shifted at the sane new times tp. The point $P'_{WMS}$ thus e.g. has to be shifted from its time t'w to t'p and the point $P''_{WMS}$ likewise to t'p. A point $P'_{DAS}$ has thus resulted from the two points $P'_{WMS}$ and $P''_{WMS}$. Depending on the frequency and the amplitude of the sinusoidal progression S, that is depending on the control of the laser, it is also possible that more than two measurement points $P_{WMS}$ are shifted to a single point $P_{DAS}$.

Figure 9:
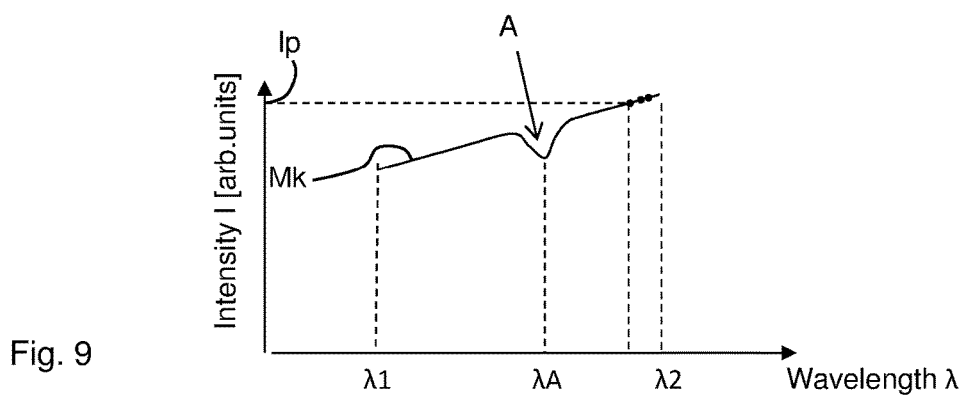
FIG. 9 a qualitative, schematic representation of an artificial measurement curve.

An artificial measurement curve Mk, such as is shown in FIG. 9, is now constructed in the evaluation unit using the measurement points P which are displaced in this manner, which have a new "sequence" and which also include a respective intensity value. The artificial measurement curve Mk then shows an absorption at the point λA and is now evaluated in the evaluation unit 36 in accordance with the methods of direct absorption spectroscopy and the first concentration value in accordance with the second alternative is determined therefrom.

The invention claimed is:

1. A method of determining the concentration of a gas component, the method comprising the steps of:
   producing a light beam having a wavelength variable in a wavelength range;
   guiding the light beam through a measurement volume in which the gas component to be determined is present, wherein the gas component has an absorption in the wavelength range;
   tuning the wavelength range, for modulation of the wavelength to occur during the tuning at a modulation frequency which is higher in comparison with a rate of the tuning, resulting in a wavelength-to-time progression with a higher-frequency modulation, with the higher frequency modulation having a determining phase;
   detecting an intensity of the light beam after passing through the measurement volume;
   during the tuning, detecting measured points which contain an intensity value and which are each recorded at times which correspond to the same phasing of the higher frequency modulation;
   producing an artificial measurement curve from the detected measured points; and
   simulating the artificial measurement curve and determining a first concentration value therefrom.

2. The method in accordance with claim 1, further comprising the step of:
   producing a plurality of artificial measurement curves which each correspond to different phases.

3. The method in accordance with claim 1, further comprising the step of:
   determining the first concentration value from the artificial measurement curve in accordance with the method of direct absorption spectroscopy.

4. The method in accordance with claim 1, further comprising the steps of:
   carrying out a simulation in accordance with the method of wavelength modulation spectroscopy from the measured points and
   determining a second concentration value.

5. The method in accordance with claim 4, further comprising the step of:
   using the first and second concentration values to achieve increased safety with respect to functional safety by a validation of the values with respect to one another.

6. The method in accordance with claim 4, further comprising the step of:
   producing a common concentration value from the first and second concentration values.

7. A method of determining the concentration of a gas component, the method comprising the steps of:
   producing a light beam having a wavelength variable in a wavelength range;

guiding the light beam through a measurement volume in which the gas component to be determined is present, wherein the gas component has an absorption in the wavelength range;

tuning the wavelength range, for modulation of the wavelength to occur during the tuning at a modulation frequency which is higher in comparison with a rate of the tuning, resulting in a wavelength-to-time progression with a higher frequency modulation;

detecting the intensity of the light beam after passing through the measurement volume;

during the tuning, saving measured points which each comprise a time and an associated intensity value;

producing an artificial measurement curve from the saved measured points by shifting the measured points on the time axis;

with the shift taking place such that an artificial, linear progression results after the shift in the wavelength-to-time progression; and simulating the artificial measurement curve and determining a first concentration value therefrom.

8. The method in accordance with claim 7, further comprising the step of determining the first concentration value from the artificial measurement curve in accordance with the method of direct absorption spectroscopy.

9. The method in accordance with claim 7, further comprising the steps of:

carrying out a simulation in accordance with the method of wavelength modulation spectroscopy from the measured points and determining a second concentration value.

10. The method in accordance with claim 9, further comprising the step of:

using the first and second concentration values to achieve increased safety with respect to functional safety by a validation of the values with respect to one another.

11. The method in accordance with claim 9, further comprising the step of:

producing a common concentration value from the first and second concentration values.

12. A spectrometer comprising a light source for producing a light beam having a wavelength variable in a wavelength range;

a measurement volume in which the gas component to be determined is present and through which the light beam runs;

control means for the light source for tuning the wavelength range, for modulation of the wavelength to occur during the tuning at a modulation frequency which is higher in comparison with a rate of the tuning, resulting in a wavelength-to-time progression with a higher frequency modulation;

a light detector for detecting the intensity of the light beam after passing through the measurement volume;

storage means for saving measured points during the tuning, wherein the measured points include an intensity value and are each recorded at times which correspond to the same phasing of the modulation;

an evaluation unit which is adapted to carry out a method of determining the concentration of a gas component, the method comprising the steps of:

producing the light beam having the wavelength variable in a wavelength range;

guiding the light beam through the measurement volume in which the gas component to be determined is present and with the gas component having an absorption in the wavelength range;

tuning the wavelength range;

detecting the intensity of the light beam after passing through the measurement volume;

detecting and saving the measured points;

and the evaluation unit is further adapted to produce an artificial measurement curve from the saved measured points;

and to simulate the artificial measurement curve and to determine a first concentration value therefrom.

13. The spectrometer in accordance with claim 12, wherein the evaluation unit is configured to determine the first concentration value in accordance with the method of direct absorption spectroscopy.

14. The spectrometer in accordance with 12, wherein the light source is a laser whose emission wavelength is variable by one of a control current and a control voltage.

15. The spectrometer in accordance with claim 12, wherein the evaluation unit is further configured to carry out a simulation in accordance with the method of wavelength modulation spectroscopy and to determine a second concentration value from the measured point.

16. A spectrometer comprising a light source for producing a light beam having a wavelength variable in a wavelength range;

a measurement volume in which the gas component to be determined is present and through which the light beam runs;

control means for the light source for tuning the wavelength range, for modulation of the wavelength to occur during the tuning at a modulation frequency which is higher in comparison with a rate of the tuning, resulting in a wavelength-to-time progression with a higher frequency modulation;

a light detector for detecting the intensity of the light beam after passing through the measurement volume;

storage means for saving measured points which each comprise a time and an associated intensity value during the tuning;

an evaluation unit which is adapted to carry out a method of determining the concentration of a gas component, the method comprising the steps of:

producing the light beam having the wavelength variable in a wavelength range;

guiding the light beam through the measurement volume in which the gas component to be determined is present, with the gas component having an absorption in the wavelength range;

tuning the wavelength range;

detecting the intensity of the light beam after passing through the measurement volume;

saving the measured points which each comprise a time and the associated intensity value;

and the evaluation unit is further adapted to produce an artificial measurement curve from the saved measured points by shifting the measured points on the time axis, wherein the shift takes place such that an artificial, linear progression results after the shift in the wavelength-to-time progression;

and to simulate the artificial measurement curve and to determine a first concentration value therefrom.

17. The spectrometer in accordance with claim 16, wherein the evaluation unit is configured to determine the first concentration value in accordance with the method of direct absorption spectroscopy.

18. The spectrometer in accordance with claim 16, wherein the light source is a laser whose emission wavelength is variable by one of a control current and a control voltage.

19. The spectrometer in accordance with claim 16, wherein the evaluation unit is further configured to carry out a simulation in accordance with the method of wavelength modulation spectroscopy and to determine a second concentration value from the measured point.

* * * * *

UNITED STATES PATENT AND TRADEMARK OFFICE
CERTIFICATE OF CORRECTION

PATENT NO. : 9,970,867 B2  
APPLICATION NO. : 15/223726  
DATED : May 15, 2018  
INVENTOR(S) : Thomas Beyer and Julian Edler It is certified that error appears in the above-identified patent and that said Letters Patent is hereby corrected as shown below:

In the Claims

Claim 1, Column 8, Line 28, please delete the phrase "having a determining phase" and replace with "having a predetermined phase".

Signed and Sealed this  
Twenty-sixth Day of June, 2018

Andrei Iancu  
*Director of the United States Patent and Trademark Office*